US006150405A

United States Patent [19]
Proctor

[11] Patent Number: 6,150,405
[45] Date of Patent: *Nov. 21, 2000

[54] HAIR LOSS TREATMENT WITH ASCORBATES

[76] Inventor: Peter H. Proctor, 4126 SW. Freeway, Suite 1616, Houston, Tex. 77027

[ * ] Notice: This patent is subject to a terminal disclaimer.

[21] Appl. No.: 08/484,297

[22] Filed: Jun. 7, 1995

Related U.S. Application Data

[63] Continuation-in-part of application No. 08/229,374, Apr. 18, 1994, Pat. No. 5,470,876, and a continuation-in-part of application No. 08/193,228, Feb. 7, 1994, Pat. No. 5,472,687, which is a continuation-in-part of application No. 08/021,970, Feb. 24, 1993, Pat. No. 5,352,442, which is a continuation-in-part of application No. 07/149,720, Jan. 29, 1988, abandoned, which is a continuation-in-part of application No. 07/008,186, Jan. 28, 1987, abandoned, which is a continuation-in-part of application No. 06/858,050, Apr. 30, 1986, abandoned, which is a continuation-in-part of application No. 06/757,131, Jul. 18, 1985, abandoned.

[51] Int. Cl.[7] .................................................. A61K 31/34
[52] U.S. Cl. ........................................................... 514/474
[58] Field of Search .................................... 514/562, 474; 562/556; 549/315, 403

[56] References Cited

U.S. PATENT DOCUMENTS

| | | | |
|---|---|---|---|
| 2,409,754 | 10/1946 | Henze | 548/301 |
| 2,986,573 | 5/1961 | Topliss | 514/223.2 |
| 3,257,390 | 6/1966 | Patchett | 540/41 |
| 3,461,461 | 8/1969 | Anthony et al. | 544/323 |
| 3,527,864 | 9/1970 | MacMillen et al. | 425/59 |
| 3,551,554 | 12/1970 | Herschler | 424/7.1 |
| 3,749,770 | 7/1973 | Martin | 424/72 |
| 3,896,238 | 7/1975 | Smith | 514/777 |
| 4,139,619 | 2/1979 | Chidsey, III | 424/45 |
| 4,189,039 | 2/1980 | Soldati | 544/12 |
| 4,254,145 | 3/1981 | Birnbaum | 424/305 |
| 4,276,284 | 6/1981 | Brown | 424/101 |
| 4,283,386 | 8/1981 | Van Scott et al. | 424/70 |
| 4,344,941 | 8/1982 | Wiechert | 424/243 |
| 4,347,245 | 8/1982 | Shapiro | 424/241 |
| 4,367,227 | 1/1983 | Bingham | 514/178 |
| 4,444,762 | 4/1984 | Rajadhyaksha | 424/180 |
| 4,456,600 | 6/1984 | Wiechert | 424/238 |
| 4,596,812 | 6/1986 | Chidsey, III | 424/251 |
| 4,711,780 | 12/1987 | Fahim | 424/145 |
| 4,866,067 | 9/1989 | Di Schiena | 514/275 |
| 5,120,831 | 6/1992 | Pickart | 530/331 |
| 5,177,061 | 1/1993 | Pickart | 514/18 |
| 5,214,032 | 5/1993 | Pickart | 514/16 |
| 5,252,559 | 10/1993 | Kronholm | 514/18 |
| 5,256,678 | 10/1993 | Nakaguchi | 514/346 |
| 5,350,767 | 9/1994 | Hallberg et al. | 514/562 |
| 5,411,991 | 5/1995 | Shander et al. | 514/665 |

FOREIGN PATENT DOCUMENTS

| | | |
|---|---|---|
| 0027655 | 4/1981 | European Pat. Off. . |
| 0249397 | 12/1987 | European Pat. Off. . |
| 0273202 | 7/1988 | European Pat. Off. . |
| 0327263 | 8/1989 | European Pat. Off. . |
| 0415598 | 3/1991 | European Pat. Off. . |
| 0415598 | 6/1991 | European Pat. Off. . |
| 0490581 | 6/1992 | European Pat. Off. . |
| 8022644 | 1/1996 | Japan . |
| 2198132 | 6/1988 | United Kingdom . |
| 8302558 | 8/1983 | WIPO . |
| 8600616 | 1/1986 | WIPO . |
| 8700427 | 1/1987 | WIPO . |
| 9304669 | 3/1993 | WIPO . |

OTHER PUBLICATIONS

Matsumoto et al, "Promotion of Hair Growth by Applying Sulfur Amino Acids and Other Compounds to the Skin", CA 81: 176108, 1974.
Matsuno, "Oral Hair Growth Promoting Preparation", CA99: 218619, 1983.
Matsumoto et al, CA81: 176108, (1974).
Cristache et al, CA104: 56186, (1986).
Aron–Brunetiere, CA 107:242432, (1987).
Anderson, *Chemical Abstracts*, vol. 90, pp. 311K (1979).
Ando et al., *Chemical Abstracts*, 93:79872n (1980).
Bazzano et al., *Journal of American Academy of Dermatology*, vol. 15, pp. 880–883 (1986).
Berry, *Pharmacology of the Skin*, vol. 1, pp. 121–137 (1987).
Cheng et al., *Archives of Dermatological Research*, vol. 278, pp. 470–473 (1986).
Cumming et al., *Journal of American Medical Association*, vol. 237, pp. 1295–1298 (1982).
*Current Therapy*, pp. 599–603 (1984).
Dahl, *Men's Fitness*, pp. 93–95 (Feb. 1989).
Dawber, *Dermatologica*, vol. 175, suppl. 2, pp. 23–28 (1987).
DeVillez, *Archives of Dermatology*, vol. 121, pp. 197–202, (1985).
*Dermatologica*, vol. 175, suppl. 2, pp. 1–56 (Oct. 87).
Dostert et al., *Xenobiotica*, vol. 15, No. 10, pp. 799–803 (1985).
Ehman et al., *Investigative Radiology*, vol. 21, pp. 125–131 (1986).
Feelisch et al., *Evr. Journal of Pharmacology*, vol. 139, pp. 19–30 (1987).
Feelisch et al., *Evr. Journal of Pharmacology*, vol. 142, pp. 405–409 (1987).
Fiedler, *Dermatologica*, vol. 175, suppl. 2, pp. 29–35 (1987).
Fox et al., *Annals of the New York Academy of Sciences*, vol. 411, pp. 14–19 (1983).

(List continued on next page.)

*Primary Examiner*—Deborah C. Lambkin
*Attorney, Agent, or Firm*—Daniel N. Lundeen

[57] ABSTRACT

A method for treating hair loss by repeated topical application of a ASCORBATES compound, a flavine or another hydroxyl radical scavenger.

8 Claims, No Drawings

OTHER PUBLICATIONS

Goffman et al., *International Journal of Radiation, Oncology, Biology and Physics*, vol. 22, pp. 803–806 (Nov. 4, 1992).

Headington, *Current Therapeutic Research*, vol. 36, pp. 1098–1105 (1984).

Hearse et al., *Circulation Research*, vol. 60, pp. 375–383 (1987).

Herschler, *Chemical Abstracts*, vol. 78, pp. 115239 (1973).

Ignarro et al. *Biochemica et. Biophysica Acta*, vol. 631, pp. 221–231 (1980).

J., *Soc. Cosmetology Chem.*, (Italy) vol. 33, pp. 95–96 (Mar./Apr. 1982).

*Journal of American Medical Association*, vol. 260, No. 20 (1988).

Karlsson et al., *Journal of Cyclic Nucleotide and Protein Res.*, vol. 10, No. 4, pp. 309–315 (1985).

Kvedar, *Journal of American Academic Dermatology*, vol. 12, pp. 215–225 (1985).

*Longevity*, vol. 2, No. 3, p. 26 (Jan. 1988).

Lucky, *Archives of Dermatology*, vol. 121, pp. 57–62 (1985).

Messina, *Current Therapeutic Research*, vol. 34, pp. 319–324 (1983).

Messina, *Curernt Therapeutic Research*, vol. 38, pp. 269–282 (1985).

Mitchell et al., IBC USA Conference, South Natick, MA (Jun. 27, 1991).

Mittal et al., *Proc. of National Academy of Science*, USA, vol. 74, No. 10, pp. 4360–4364 (1977).

Palmer et al., *Nature*, vol. 327, pp. 524–526 (Jun. 11, 1987).

Parrett et al., *Journal of Pharmacology*, vol. 91, pp. 49–59 (1987).

*Physician's Desk Reference*, pp. 883,977–978, 1782–1785, 1961 (1983).

Proctor et al., *Physiological Chemistry and Physics in Medical NMR*, vol. 16, pp. 175–195 (1984).

Ross, U.S. Department of Commerce, National Bureau of Standards, *Publication NSRDS–NBS59* (Jan. 1977).

Sekura, *Advances of Biology and Skin*, vol. XII, pp. 257–269, (1972).

Shapiro, et al., *Journal of Clinical Endocrinology and Metabolism*, vol. 51, pp. 429–430 (1980).

Stewart, *International Journal of Dermatology*, vol. 17, pp. 167–179 (1978).

Thompson, *Federal Drug Administration Consumer*, pp. 10 and 12 (Mar. 10, 1981).

Tiffany–Castiglion, *Biochenical Pharmacology*, vol. 31, No. 2, pp. 181–188 (1982).

Torre (Ed.), *Annals of the New York Academy of Sciences*, vol. 411, Table of Contents (1983).

Vermorken, *Acta Dermatovener* (Stockholm), vol. 63, pp. 268–269 (1982).

Voorhees (Ed.), *Dermatologica*, vol. 175, suppl. 2, pp. 1–56 (1987).

Watanabe et al., *Archives of Dermatological Research*, vol. 278, pp. 470–473 (1986).

Weissmann, *Archives of Dermatology*, vol. 121, pp. 57–62 (1985).

Yoshioka et al. *Archives of Dermatological Research*, vol. 278, pp. 177–183 (1986).

Proctor, *Archives of Dermatology*, p. 1146 (Aug. 1989).

HAIR LOSS TREATMENT WITH ASCORBATES

CROSS-REFERENCE TO RELATED APPLICATIONS

This application is a continuation-in-part of application Ser. No. 08/229,374, filed Apr. 18, 1994, U.S. Pat. No. 5,470,876 and Ser. No. 08/193,228, filed Feb. 7, 1994, U.S. Pat. No. 5,473,687 which are continuations-in-part of Ser. No. 08/021,970, filed Feb. 24, 1993, now U.S. Pat. No. 5,352,442; which is a continuation-in-part of Ser. No. 07/149,720, filed Jan. 29, 1988, abandoned; which is a continuation-in-part of application Ser. No. 07/008,186, filed Jan. 28, 1987, abandoned; which is a continuation-in-part of application Ser. No. 06/858,050, Apr. 30, 1986, abandoned; which is a continuation-in-part of application Ser. No. 06/757,131, Jul. 18, 1985, abandoned.

FIELD OF THE INVENTION

This invention relates to the use of sulfhydryl compounds such as thioproline, homocysteine, cysteine and/or N-acetylcysteine for treating hair loss.

BACKGROUND OF THE INVENTION

Recently, several anti-alopecia agents such as minoxidil and cyoctol have gained attention. However, most of these anti-alopecia agents are only minimally effective in some cases and/or can cause adverse dermatological or systemic reactions. Thus, the search continues for new, safer and more effective anti-alopecia agents.

SUMMARY OF THE INVENTION

Applicant has discovered that sulfhydryl compounds such as thioproline, homocysteine, cysteine and N-acetyl-L-cysteine have restorative properties in the body and can be administered, for example, as a anti-alopecia agent to stimulate cosmetic hair growth or as a protectant to minimize hair loss during cancer treatments known to induce hair loss.

DETAILED DESCRIPTION OF THE INVENTION

In the present invention, sulfhydryl compounds are compounded in a pharmaceutical formulation or carrier for topical or internal administration. The pharmaceutical carrier in which the sulfhydryl is generally substantially homogeneously dispersed can be an aqueous dispersion or suspension, or a water-in-oil or oil-in-water emulsion depending on the administration route. Topical pharmaceutical carriers which can be mentioned include water, urea, alcohols and glycols such as methanol, ethanol, propanol, butanol, ethylene glycol, propylene glycol, and the like. Internally administered pharmaceutical carriers typically include water and ethanol.

Suitable water-in-oil emulsions are commercially available under the designations Aquaphor, cold cream, Eucerin, hydrous lanolin, Hydrosorb hydrophilic petrolatum, Nivea, Polysorb, Qualatum and Velvachol. Suitable oil-in-water emulsions are available commercially under the designations acid mantle cream, Almay emulsion cream, Cetaphil, Dermabase, Dermavan, hydrophilic ointment, Keri cream, Lubriderm cream, Multibase cream, Neobase cream, Unibase cream, Vanibase cream and Wibi. The carrier may further contain various other emollients, emulsifiers, water, perfumes, colorants, preservatives, and the like. The topical formulation is in the form of a cream, lotion, shampoo, cream rinse, or the like.

The sulfhydryls used in the present invention include pharmaceutically acceptable sulfhydryl compounds and their derivatives such as esters, peptides and nitrosoderivatives. Exemplary sulfhydryls include cysteine, homocysteine, acetylcysteine, glutathione, cysteamine, 2-thiobarbituric acid, dithiothreitol, penicillamine, N-acetylpenicillamine, taurine, cysteamide, diethyidithiocarbamate salts, L-2-oxothiazolidine-4-carboxylate and its hydrocarbyl esters, dimethylthiourea, thiosalicylic acid, ethiophos, spironolactone, and the like. These can be used alone or in combination.

Other hair growth stimulants which can be used with or in place of the sulfhydryls are flavines such as, for example, troxerutin, quercetin, myricetin, rutin, quercitrin, meciadonol, 7,8-benzoflavine, catechin, and the like; and other hydroxyl radical scavengers such as, for example, ascorbic acid and ascorbyl esters such as ascorbyl palmitate, uric acid, methylated uric acids and purines, butylated hydroxytoluene (BHT), butylated hydroxyanisole (BHA), 5-aminosalicylic acid, sulfapyridine, sulfasalazine, "Bioharmony," ellagic acid, mannitol, deferoxamine, benzoate, ethoxyquin, methoxyquin, pentetic acid, neocuproine, cytokinins, ubiquinones, allopurinol, tyrosine, piroxicam, lazaroids, and the like.

Effective amounts of the sulfhydryl generally range from about 0.01 to about 20% by weight of the administered composition, more preferably from about 0.1 to about 10% by weight, most preferably from about 0.5 to about 3% by weight, but more or less can be present in the composition depending on the particular formulation and the treatment conditions.

The sulfhydryls can be used alone or in combination with other additaments which are available to enhance the function of hair growth stimulation such as, for example, the hydroxyl radical scavengers, antiandrogens and others described in International Publication No. WO 87/00427 (International Application No. PCT/US86/01393) published on Jan. 29, 1987; and European Patent Application No. 89300785.6, Publication No. 0327263/A1, published Aug. 9, 1989; both of which are hereby incorporated in their entirety herein as though fully set forth verbatim, including reference therein to the publication of Ross & Ross, "Selected Specific Rates of Reactions of Transients From Water In Aqueous Solution. III. Hydroxyl Radical and Pure Hydroxyl Radicals and Their Radical Ions," National Standard Reference Data Series, National Bureau of Standards, 59 (1977), which is also incorporated herein by reference.

According to the present invention, the sulfhydryl can be administered to the skin to be treated, such as the scalp. Depending on the type of hair loss or alopecia being treated and the conditions thereof, the stimulation of hair growth can usually be obtained by topical application, preferably repeated daily application for a period of 3–6 months. The utility of topically applied sulfhydryls is not limited thereto, however, and the stimulation of hair growth can include an increased rate of growth, increased hair diameter, follicular neogenesis, and the like, inhibiting hair loss or alopecia from progressing, for example, in male pattern baldness, or during the course of treatment with other therapeutic agents known to induce hair loss, such as chemotherapy or radiation therapy in cancer treatment as well as a restorative for increasing the overall relative health of the skin and other treated organs.

The invention is illustrated by way of the following examples:

EXAMPLE 1

A cysteine shampoo is prepared by mixing 0.5 g of N-acetylcysteine in 500 ml of a commercially available shampoo. The shampoo is used daily on the scalp for normal shampooing of the hair for a period of from 3 to 6 months to obtain cosmetic hair growth.

EXAMPLE 2

An ascorbate shampoo is prepared by mixing 0.5 g of ascorbyl palmitate in 500 ml of a commercially available shampoo. The shampoo is used daily on the scalp for normal shampooing of the hair for a period of from 3 to 6 months to obtain cosmetic hair growth.

The invention is described above and illustrated herein with reference to specific chemical formulas, preparations and therapeutic and cosmetic applications. Many variations and modifications will become apparent to those skilled in the art in view of the foregoing disclosure. It is intended that the following claims are not to be limited thereby, and are to be construed in accordance with the spirit and scope thereof.

What is claimed is:

1. A method for stimulating hair growth comprising repeatedly applying in a topical pharmaceutical carrier to skin a hydroxyl radical scavenger selected from the group consisting of ascorbic acid and ascorbyl esters, in an amount effective to stimulate hair growth.

2. The method of claim 1, comprising topical application of ascorbic acid.

3. The method of claim 1, comprising topical application of an ascorbyl ester.

4. The method of claim 1, comprising topical application of ascorbyl palmitate.

5. In a method for stimulating hair growth comprising repeated application to skin of a topical pharmaceutical carrier comprising a hair growth stimulant, the improvement wherein the carrier comprises therein a hydroxyl radical scavenger selected from the group consisting of ascorbic acid and ascorbyl esters, in an amount effective to stimulate hair growth.

6. The improvement of claim 5, comprising topical application of ascorbic acid.

7. The improvement of claim 5, comprising topical application of ascorbyl ester.

8. The improvement of claim 5, comprising topical application of ascorbyl palmitate.

* * * * *